United States Patent
Jacobson et al.

(10) Patent No.: US 9,272,089 B2
(45) Date of Patent: *Mar. 1, 2016

(54) DIFFERENTIAL PRESSURE BASED FLOW SENSOR ASSEMBLY FOR MEDICATION DELIVERY MONITORING AND METHOD OF USING THE SAME

(71) Applicant: Hospira, Inc., Lake Forest, IL (US)

(72) Inventors: James D Jacobson, Lindenhurst, IL (US); Brian Barclay, Pleasant Prairie, WI (US); Ryan R Brumund, Libertyville, IL (US); Steven T Cho, Chandler, AZ (US); Hrishikesh Choudhury, Gurnee, IL (US); Marwan A Fathallah, Mundelein, IL (US); Tom Johnson, Gurnee, IL (US); Patrick B Keely, Tacoma, WA (US); Mohammad M Khair, Streamwood, IL (US); Michael G Lowery, Wildwood, IL (US); Frank Walsworth, Grayslake, IL (US); John S Ziegler, Arlington Heights, IL (US)

(73) Assignee: HOSPIRA, INC., Lake Forest, IL (US)

( * ) Notice: Subject to any disclaimer, the term of this patent is extended or adjusted under 35 U.S.C. 154(b) by 332 days.

This patent is subject to a terminal disclaimer.

(21) Appl. No.: 13/850,126

(22) Filed: Mar. 25, 2013

(65) Prior Publication Data

US 2013/0218133 A1     Aug. 22, 2013

Related U.S. Application Data

(63) Continuation of application No. 12/335,128, filed on Dec. 15, 2008, now Pat. No. 8,403,908.

(60) Provisional application No. 61/014,298, filed on Dec. 17, 2007.

(51) Int. Cl.
*A61M 5/172* (2006.01)
*A61M 5/168* (2006.01)
*G01F 1/42* (2006.01)

(52) U.S. Cl.
CPC ........... *A61M 5/172* (2013.01); *A61M 5/16804* (2013.01); *A61M 5/16854* (2013.01); *A61M 5/16886* (2013.01); *G01F 1/42* (2013.01)

(58) Field of Classification Search
CPC .................... A61M 5/16804; A61M 5/16854; A61M 5/16886; A61M 5/17; A61M 5/172; G01F 1/42; G01F 1/4222
See application file for complete search history.

(56) References Cited

U.S. PATENT DOCUMENTS

| 4,195,515 | A | 4/1980 | Smoll |
| 4,240,294 | A | 12/1980 | Grande |

(Continued)

FOREIGN PATENT DOCUMENTS

| DE | 10249238 | 5/2004 |
| EP | 0337092 A2 | 10/1989 |

(Continued)

OTHER PUBLICATIONS

Alan F. Merry, Craig S. Webster and Daniel J. Matthew et al. A New Safety-Oriented Integrated Drug Administration and Automated Anesthesia Record System. Anesth Analg 2001;93:385-90.

(Continued)

*Primary Examiner* — Kevin C Sirmons
*Assistant Examiner* — Imani Hayman
(74) *Attorney, Agent, or Firm* — Michael R. Crabb

(57) ABSTRACT

A differential pressure based flow sensor assembly and method of using the same to determine the rate of fluid flow in a fluid system. The sensor assembly comprises a disposable portion and a reusable portion. A flow restricting element is positioned along a fluid flow passage between an inlet and an outlet. The disposable portion further has an upstream fluid pressure membrane and a downstream fluid pressure membrane. The reusable portion has an upstream fluid pressure sensor and a downstream fluid pressure sensor. The upstream fluid pressure sensor senses the upstream fluid pressure at a location within the fluid flow passage between the inlet and the flow restricting element. The downstream fluid pressure sensor senses the downstream fluid pressure at a location within the fluid flow passage between the flow restricting element and the outlet. The process utilizes output of the sensors to calculate the flow rate of the fluid.

19 Claims, 10 Drawing Sheets

(56) References Cited

U.S. PATENT DOCUMENTS

| | | |
|---|---|---|
| 4,261,356 A | 4/1981 | Turner et al. |
| 4,343,316 A | 8/1982 | Jespersen |
| 4,758,228 A | 7/1988 | Williams |
| 4,856,339 A | 8/1989 | Williams |
| 4,881,413 A | 11/1989 | Georgi et al. |
| 4,938,079 A | 7/1990 | Goldberg |
| 4,947,856 A | 8/1990 | Beard |
| 5,211,626 A | 5/1993 | Frank et al. |
| 5,242,406 A | 9/1993 | Gross et al. |
| 5,287,851 A | 2/1994 | Beran et al. |
| 5,325,728 A | 7/1994 | Zimmerman et al. |
| 5,417,119 A | 5/1995 | Smoll |
| 5,417,395 A | 5/1995 | Fowler et al. |
| 5,450,758 A | 9/1995 | Smoll |
| 5,463,906 A | 11/1995 | Spani et al. |
| 5,611,784 A | 3/1997 | Barresi et al. |
| 5,628,309 A | 5/1997 | Brown |
| 5,651,775 A | 7/1997 | Walker et al. |
| 5,672,832 A | 9/1997 | Cucci et al. |
| 5,697,916 A | 12/1997 | Schraga |
| 5,722,417 A | 3/1998 | Garbe |
| 5,728,074 A | 3/1998 | Castellano et al. |
| 5,752,918 A | 5/1998 | Fowler et al. |
| 5,758,643 A | 6/1998 | Wong et al. |
| 5,805,455 A | 9/1998 | Lipps |
| 5,848,971 A | 12/1998 | Fowler et al. |
| 5,891,051 A | 4/1999 | Han et al. |
| 5,904,666 A | 5/1999 | DeDecker et al. |
| 5,944,660 A | 8/1999 | Kimball et al. |
| 5,947,911 A | 9/1999 | Wong et al. |
| 6,068,615 A | 5/2000 | Brown et al. |
| 6,237,398 B1 | 5/2001 | Porat et al. |
| 6,250,132 B1 | 6/2001 | Drzewiecki |
| 6,270,455 B1 | 8/2001 | Brown |
| 6,272,934 B1 | 8/2001 | Rajan et al. |
| 6,277,099 B1 | 8/2001 | Strowe et al. |
| 6,349,740 B1 | 2/2002 | Cho et al. |
| 6,385,505 B1 | 5/2002 | Lipps |
| 6,386,050 B1 | 5/2002 | Yin et al. |
| 6,445,053 B1 | 9/2002 | Cho |
| 6,482,185 B1 | 11/2002 | Hartmann |
| 6,558,125 B1 | 5/2003 | Futterknecht |
| 6,568,416 B2 | 5/2003 | Tucker et al. |
| 6,578,435 B2 | 6/2003 | Gould et al. |
| RE38,189 E | 7/2003 | Walker et al. |
| 6,589,229 B1 | 7/2003 | Connelly et al. |
| 6,609,047 B1 | 8/2003 | Lipps |
| D481,121 S | 10/2003 | Evans |
| D485,356 S | 1/2004 | Evans |
| 6,685,668 B1 | 2/2004 | Cho et al. |
| 6,685,678 B2 | 2/2004 | Evans et al. |
| 6,722,211 B1 | 4/2004 | Ciobanu et al. |
| 6,760,643 B2 | 7/2004 | Lipps |
| 6,813,964 B1 | 11/2004 | Clark et al. |
| 6,920,795 B2 | 7/2005 | Bischoff et al. |
| 6,929,619 B2 | 8/2005 | Fago et al. |
| 6,932,796 B2 | 8/2005 | Sage et al. |
| 6,935,192 B2 | 8/2005 | Sobek et al. |
| 6,964,204 B2 | 11/2005 | Clark et al. |
| 6,975,922 B2 | 12/2005 | Duncan et al. |
| 6,981,960 B2 | 1/2006 | Cho et al. |
| 7,021,148 B2 | 4/2006 | Kuhn et al. |
| 7,059,184 B2 | 6/2006 | Kanouda et al. |
| 7,074,209 B2 | 7/2006 | Evans et al. |
| 7,082,843 B2 | 8/2006 | Clark et al. |
| 7,096,729 B2 | 8/2006 | Repko et al. |
| 7,115,113 B2 | 10/2006 | Evans et al. |
| 7,161,488 B2 | 1/2007 | Frasch |
| 7,162,290 B1 | 1/2007 | Levin |
| 7,162,927 B1 | 1/2007 | Selvan et al. |
| 7,174,789 B2 | 2/2007 | Orr et al. |
| 7,197,943 B2 | 4/2007 | Lee et al. |
| 7,415,895 B2 | 8/2008 | Kurisaki et al. |
| 7,503,903 B2 | 3/2009 | Carlisle et al. |
| 7,571,024 B2 | 8/2009 | Duncan et al. |
| 7,693,697 B2 | 4/2010 | Westenskow et al. |
| 7,775,126 B2 | 8/2010 | Eckhardt |
| 7,775,127 B2 | 8/2010 | Wade |
| 2002/0038392 A1 | 3/2002 | De La Huerga |
| 2002/0099334 A1 | 7/2002 | Hanson et al. |
| 2003/0018308 A1 | 1/2003 | Tsai |
| 2003/0065537 A1 | 4/2003 | Evans |
| 2004/0082918 A1 | 4/2004 | Evans et al. |
| 2004/0193325 A1 | 9/2004 | Bonderud et al. |
| 2004/0225409 A1 | 11/2004 | Duncan et al. |
| 2004/0232219 A1 | 11/2004 | Fowler |
| 2005/0204828 A1 | 9/2005 | Lee et al. |
| 2006/0117856 A1 | 6/2006 | Orr et al. |
| 2006/0181695 A1 | 8/2006 | Sage, Jr. |
| 2006/0260416 A1 | 11/2006 | Sage et al. |
| 2007/0060872 A1 | 3/2007 | Hall et al. |
| 2007/0129618 A1 | 6/2007 | Goldberger et al. |
| 2007/0179436 A1 | 8/2007 | Braig et al. |

FOREIGN PATENT DOCUMENTS

| | | |
|---|---|---|
| JP | 2001301118 A | 5/1989 |
| JP | 2011128344 A | 5/1999 |
| JP | 2000510575 A | 2/2000 |
| JP | 2005524081 A | 3/2005 |
| JP | 2005524081 A | 8/2005 |
| JP | 2007071695 | 3/2007 |
| WO | 9730333 A | 8/1997 |
| WO | 0209795 A | 2/2002 |
| WO | 0227276 A2 | 4/2002 |
| WO | 03093780 A1 | 11/2003 |
| WO | 2005030489 A1 | 4/2005 |
| WO | 2005082450 A1 | 9/2005 |
| WO | 2005118015 A1 | 12/2005 |

OTHER PUBLICATIONS

Dec. 2005 Advertisement from SensorONE Ltd for the Series PD-39 X Differential Pressure Transmitter.
2005 Advertisement form BARD for the CritiCore Monitor.
Office Action, Japanese Patent Office, application No. JP2010539718T, issued Jan. 8, 2013.

DIFFERENTIAL PRESSURE BASED FLOW SENSOR ASSEMBLY FOR MEDICATION DELIVERY MONITORING AND METHOD OF USING THE SAME

CROSS REFERENCE TO RELATED APPLICATIONS

This application is a continuation of U.S. application Ser. No. 12/335,128, filed Dec. 15, 2008 now U.S. Pat. No. 8,403, 908, which claims priority based upon U.S. Provisional Application Ser. No. 61/014,298 filed Dec. 17, 2007, which is expressly incorporated herein by reference in its entirety.

TECHNICAL FIELD

The present invention generally relates to a differential pressure based flow sensor assembly and method for monitoring medication delivery utilizing a system containing the differential pressure based flow sensor assembly, and more particularly to a differential pressure based flow sensor assembly that has a disposable portion and a reusable portion.

BACKGROUND

Modern medical devices, including medical pumps, are increasingly being controlled by microprocessor based systems to deliver fluids, solutions, medications, and drugs to patients. A typical control for a medical pump includes a user interface enabling a medical practitioner to enter the dosage of fluid to be delivered, the rate of fluid delivery, the duration, and the volume of a fluid to be infused into a patient. Typically, drug delivery is programmed to occur as a continuous infusion or as a single bolus dose.

It is common for a plurality of medications to be infused to a patient by using a multi-channel infusion pump or using a plurality of single channel infusion pumps where a different fluid is administered from each channel. Another method of delivering multiple medications to a patient is to deliver a first medication using an infusion pump, and additional medications through single bolus doses.

When delivering medications through single bolus doses it is important to verify that correct medications are being delivered to the patient as well as to verify that the correct amount of medication is being delivered to the patient. Typically a caregiver simply manually notes on the patient's paper chart the amount of medication delivered via a bolus dose, and that information may later be entered into a patient's record electronically. Thus, human error may lead to an accidental overdose or underdose of a medication, while a caregiver believes that a proper dose was delivered. In addition to an error in medication dosing, it is also possible that human error may result in the failure to record the medication delivered during a single bolus dose. Thus, it is possible that a patient's medical records may not reflect every medication that patient has been given. A sensor within the IV line capable of measuring a wide range of fluids and flow rates would be helpful in documenting the flow rate and volume of every medication the patient is given through that line. Further, it is desirable to provide a robust flow rate sensing methodology that is low cost and in particular introduces low incremental cost to the disposable medication delivery tubing set. Further, it is desirable to provide a flow rate sensing methodology that is capable of accurately sensing the flow rate of fluids that have a range of physical properties, including fluid viscosity, which may not be known precisely. Therefore, a need exists for a differential pressure based flow sensor system adapted for monitoring medication delivery.

SUMMARY

According to one embodiment, a differential pressure based flow sensor assembly adapted to determine the rate of a fluid system comprises a disposable portion, and a reusable portion. The disposable portion has a body that defines a fluid flow passage that forms an inlet and an outlet. A flow restricting element is positioned along the fluid flow passage between the inlet and the outlet. The disposable portion further has an upstream fluid pressure membrane at a location within the fluid flow passage between the inlet and the flow restricting element. A downstream fluid pressure membrane is located in the fluid flow passage between the flow restricting element and the outlet of the disposable portion.

The reusable portion has an upstream fluid pressure sensor and a downstream fluid pressure sensor. The upstream fluid pressure sensor senses the upstream fluid pressure at a location within the fluid flow passage between the inlet and the flow restricting element. The upstream fluid pressure sensor is positioned to determine the fluid pressure at the upstream fluid pressure membrane.

The downstream fluid pressure sensor senses the downstream fluid pressure at a location within the fluid flow passage between the flow restricting element and the outlet. The downstream fluid pressure sensor is positioned to determine the fluid pressure at the downstream fluid pressure membrane.

According to another embodiment, a disposable assembly for use with a differential pressure based fluid flow assembly comprises a body, a flow restricting element, an upstream fluid pressure membrane, and a downstream fluid pressure membrane. The body defines a fluid flow passage that forms an inlet and an outlet. The flow restricting element is positioned between the inlet and the outlet within the fluid flow passage. The upstream fluid pressure membrane is located within the fluid flow path between the inlet and the flow restricting element. The downstream fluid pressure membrane is located within the fluid flow path between the flow restricting element and the outlet.

According to one embodiment, a method determines a fluid flow rate in a fluid flow system. The method provides a differential pressure based flow sensor assembly. The sensor assembly comprises a disposable portion, and a reusable portion. The disposable portion has a body that defines a fluid flow passage that forms an inlet and an outlet. A flow restricting element is positioned along the fluid flow passage between the inlet and the outlet. The disposable portion further has an upstream fluid pressure membrane at a location within the fluid flow passage between the inlet and the flow restricting element. A downstream fluid pressure membrane is located in the fluid flow passage between the flow restricting element and the outlet of the disposable portion. The reusable portion has an upstream fluid pressure sensor and a downstream fluid pressure sensor.

The upstream fluid pressure sensor senses the upstream fluid pressure at a location within the fluid flow passage between the inlet and the flow restricting element. The upstream fluid pressure sensor is positioned to determine the fluid pressure at the upstream fluid pressure membrane. The downstream fluid pressure sensor senses the downstream fluid pressure at a location within the fluid flow passage between the flow restricting element and the outlet.

The downstream fluid pressure sensor is positioned to determine the fluid pressure at the downstream fluid pressure membrane. Fluid is directed through the fluid flow passage. The process calculates the fluid flow rate based on a pressure difference between an output of the upstream fluid pressure sensor and an output of the downstream fluid pressure sensor.

According to a further embodiment, a fluid delivery system for delivering the fluid medication from a first source to a patient, and for measuring the flow rate of the fluid, comprises an infusion pump, a differential pressure based flow sensor assembly, and a processor. The infusion pump selectively varies a rate of flow of the first medication from the first source through a fluid line. The differential pressure based flow sensor assembly determines the flow rate of the first medication within the fluid line.

The sensor assembly has a disposable portion, and a reusable portion. The disposable portion has a body that defines a fluid flow passage that forms an inlet and an outlet. A flow restricting element is positioned along the fluid flow passage between the inlet and the outlet. The disposable portion further has an upstream fluid pressure membrane at a location within the fluid flow passage between the inlet and the flow restricting element. A downstream fluid pressure membrane is located in the fluid flow passage between the flow restricting element and the outlet of the disposable portion.

The reusable portion has an upstream fluid pressure sensor and a downstream fluid pressure sensor. The upstream fluid pressure sensor senses the upstream fluid pressure at a location within the fluid flow passage between the inlet and the flow restricting element. The upstream fluid pressure sensor is positioned to determine the fluid pressure at the upstream fluid pressure membrane.

The downstream fluid pressure sensor senses the downstream fluid pressure at a location within the fluid flow passage between the flow restricting element and the outlet. The downstream fluid pressure sensor is positioned to determine the fluid pressure at the downstream fluid pressure membrane.

The processor is adapted to control the infusion pump by varying the rate of flow of the first medication based on information provided by the differential pressure based flow sensor assembly. The processor is also adapted to determine the amount of the first medication provided to the patient.

Yet another process delivers medication to a patient using a differential pressure based flow sensor assembly to determine the flow rate of a first medication within a fluid line. The sensor assembly comprises a disposable portion, and a reusable portion. The disposable portion has a body that defines a fluid flow passage that forms an inlet and an outlet. A flow restricting element is positioned along the fluid flow passage between the inlet and the outlet. The disposable portion further has an upstream fluid pressure membrane at a location within the fluid flow passage between the inlet and the flow restricting element. A downstream fluid pressure membrane is located in the fluid flow passage between the flow restricting element and the outlet of the disposable portion.

The reusable portion has an upstream fluid pressure sensor and a downstream fluid pressure sensor. The upstream fluid pressure sensor senses the upstream fluid pressure at a location within the fluid flow passage between the inlet and the flow restricting element. The upstream fluid pressure sensor is positioned to determine the fluid pressure at the upstream fluid pressure membrane. The downstream fluid pressure sensor senses the downstream fluid pressure at a location within the fluid flow passage between the flow restricting element and the outlet. The downstream fluid pressure sensor is positioned to determine the fluid pressure at the downstream fluid pressure membrane.

The process senses the flow rate of the first medication with the flow sensor assembly. An infusion pump that selectively varies the flow rate of the first medication is controlled based upon information that the flow sensor assembly provides to a processor. The process determines the amount of the first medication delivered to the patient, based upon information the flow sensor assembly provides to the processor.

A further process determines a fluid flow rate within a fluid flow system. An upstream pressure sensor is provided in a fluid flow path. A downstream pressure sensor is also provided in the fluid flow path. The process provides a flow restricting element along the fluid flow path between the upstream pressure sensor and the downstream pressure sensor. Fluid is directed through the fluid flow path. A fluid flow rate is calculated based upon the pressure difference between an output of the upstream fluid pressure sensor and an output of the downstream fluid pressure sensor.

DETAILED DESCRIPTION

Figure 1:
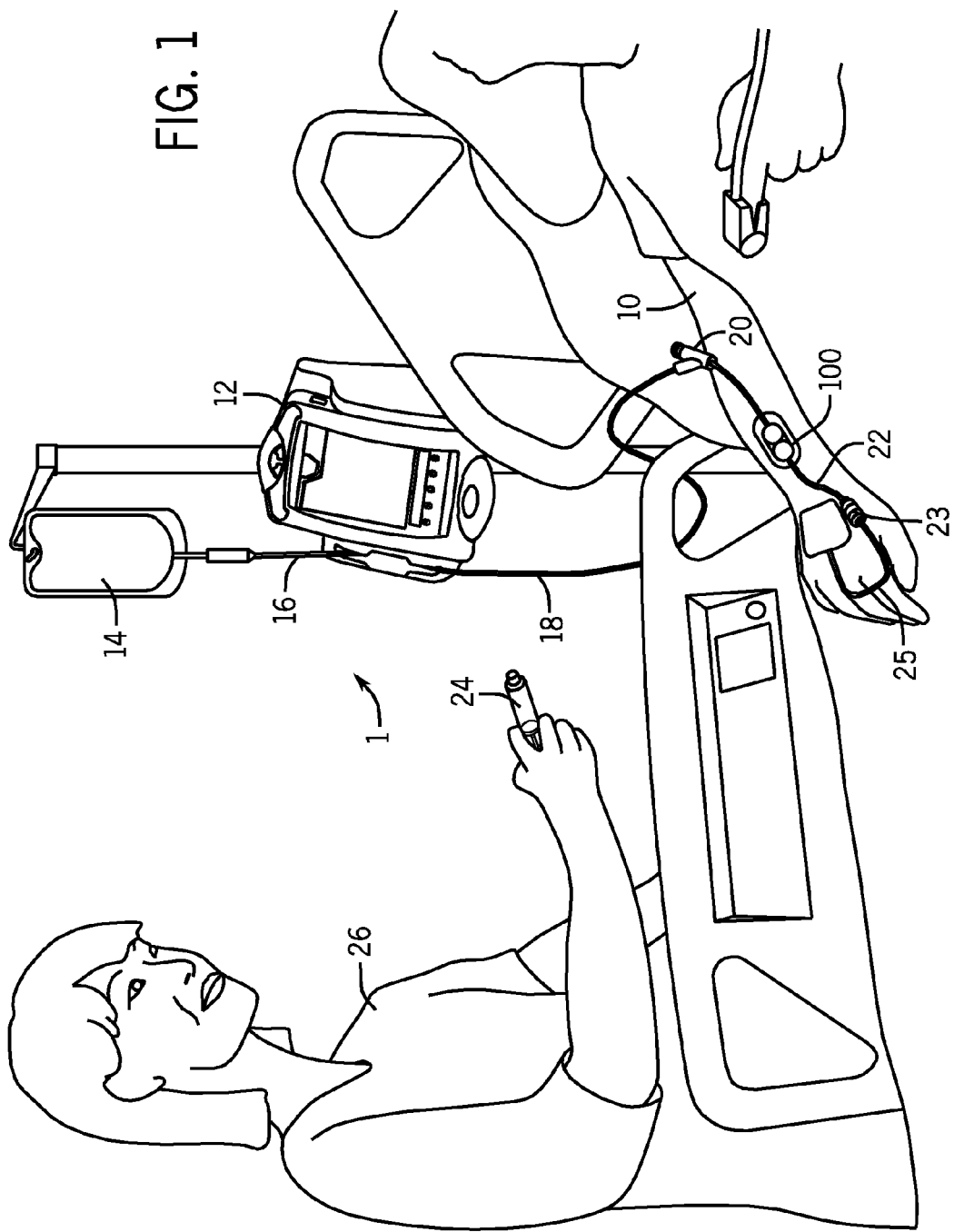
FIG. 1 is a pictorial view that illustrates a patient connected to IV line having a differential pressure based flow sensor assembly according to one embodiment.

While this invention is susceptible of embodiments in many different forms, there is shown in the drawings and will herein be described an example of the invention. The present disclosure is to be considered as an example of the principles of the invention. It is not intended to limit the broad aspect of the invention to the examples illustrated.

FIG. 1 is a pictorial representation of a patient 10 connected to a medication delivery system 1 and receiving a first medication via an infusion pump 12 from a medication reservoir 14. A first fluid line segment 16 delivers the first medication from the reservoir 14 to the infusion pump 12. The second fluid line segment 18 delivers the medication from the infusion pump 12 to a differential pressure based flow sensor assembly 100. A third fluid line segment 22 delivers the medication from the differential pressure based flow sensor 100 to the patient 10. While three fluid lines segments are described in connection with FIG. 1, it is contemplated that the number of fluid lines or line segments used in connection with the present invention may vary, and may be more or less than three fluid lines. The third fluid line segment 22 is typically connected to the patient 10 through a connector valve 23 and a patient access device such as a catheter 25.

The second fluid line segment 18 has a connection 20 adapted to receive a second medication from a second source. The connection illustrated in FIG. 1 is typically referred to as a Y-Site, although it is contemplated that other connection types and configurations may be used in connection with the present invention.

Figure 2:
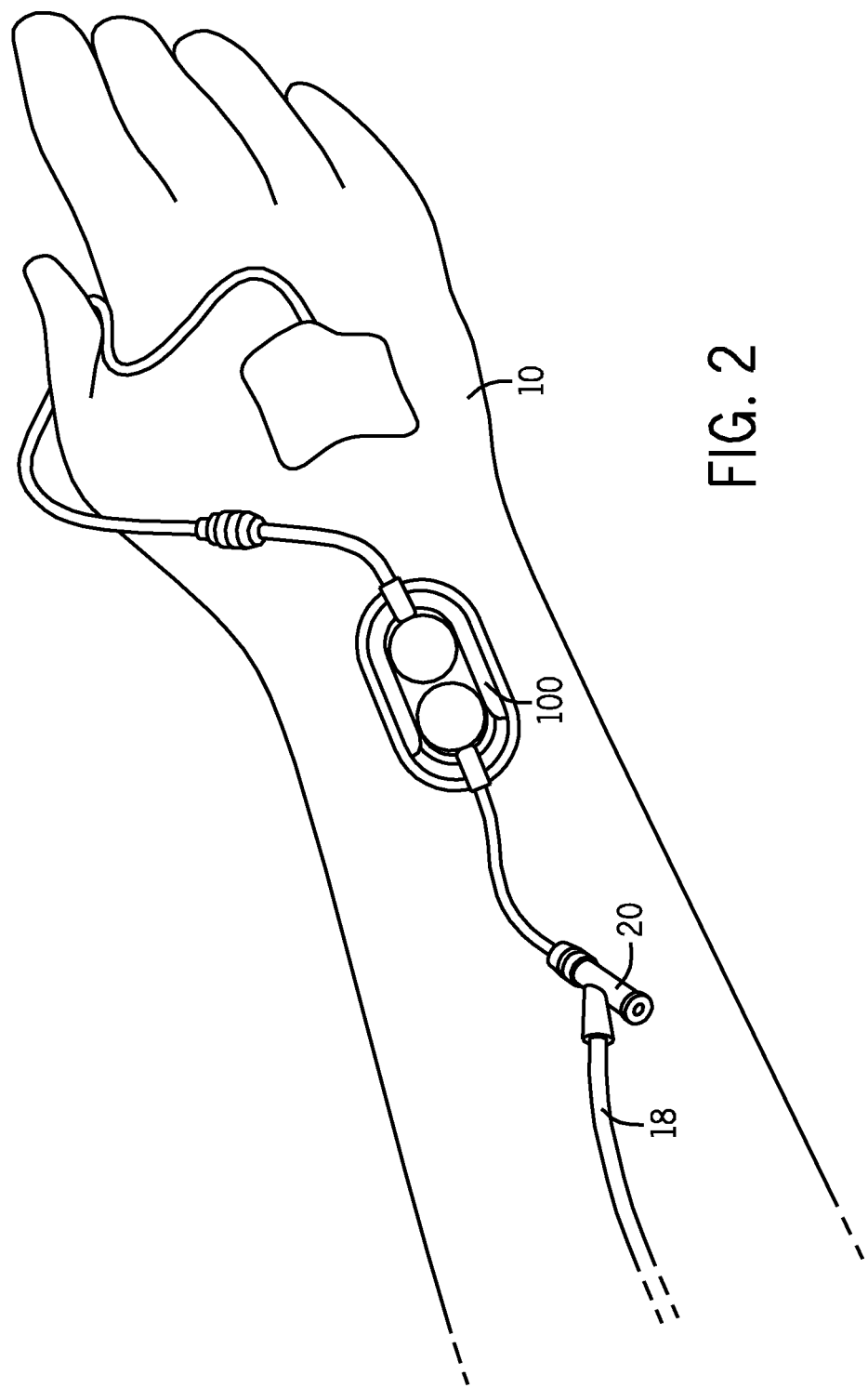
FIG. 2 shows a closer, more detailed pictorial view of the differential pressure based flow sensor assembly of the embodiment of FIG. 1.
Figure 6:
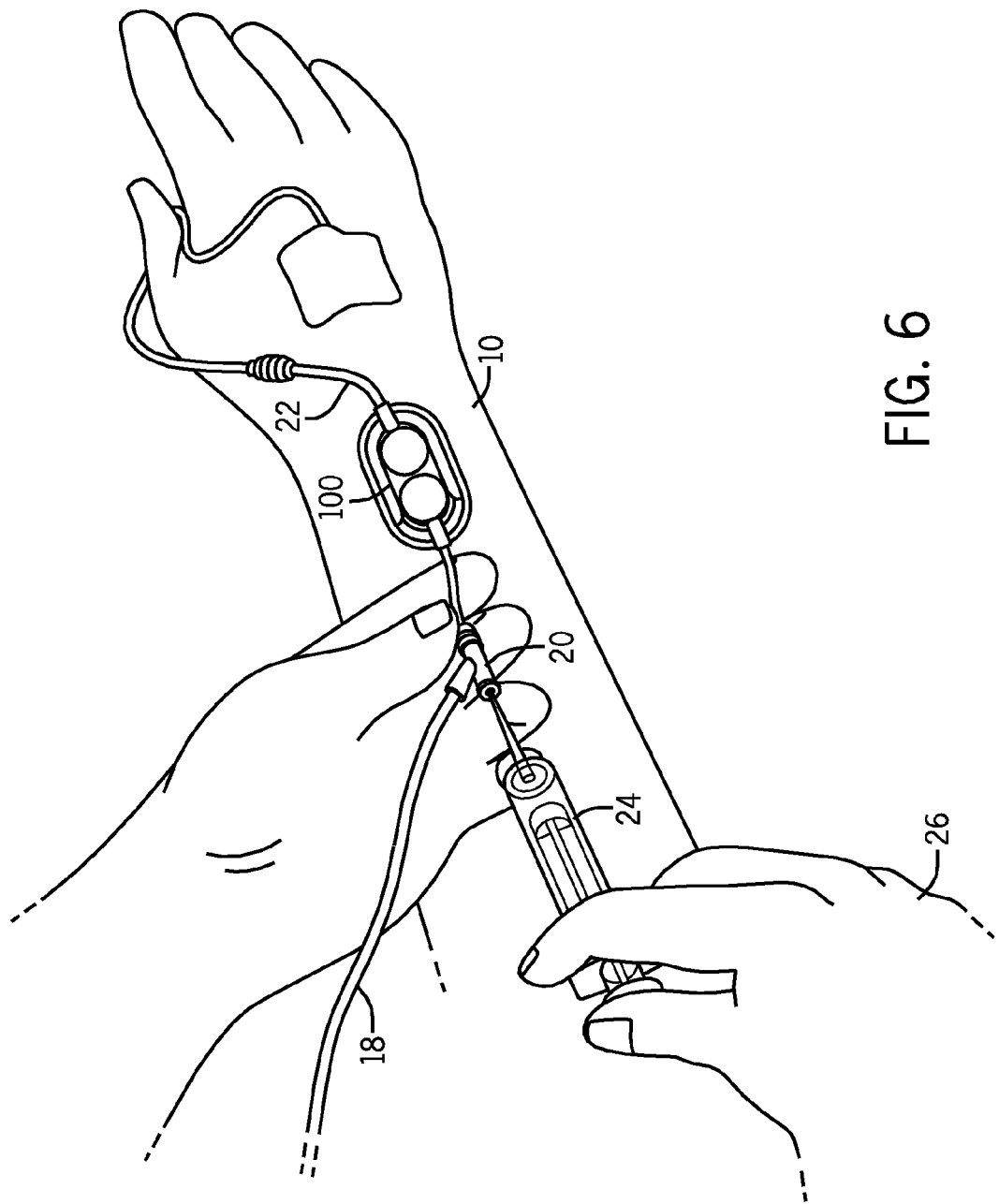
FIG. 6 is a pictorial view illustrating delivery of medication to a patient via an IV push or bolus through an IV line having the differential pressure based flow sensor assembly of FIG. 1.

The connection 20, shown in additional detail in FIG. 2, may receive a second medication from a syringe 24 in the form of a manual IV push or bolus by a caregiver 26 (see FIG. 6). It is further contemplated that the second medication may be provided in another fashion, such as from a second medication reservoir or other known medication delivery source. The medication delivery system 1 further has a differential pressure based flow sensor assembly 100. In the illustrated embodiment, the differential pressure based flow sensor assembly 100 is located downstream of the connector 20 and is secured on the patient 10. Thus, the flow sensor assembly is adapted to have both the first and the second medication pass through the sensor assembly 100. However, the sensor assembly 100 could also be disposed in any number of locations including but not limited to upstream of the fluid junction between the first and second medication, connected between the second source and the connector 20, or integrally formed on or within one of the branches of the connector 20. The flow sensor assembly 100 need not be secured to the patient 10 directly.

Figure 3:
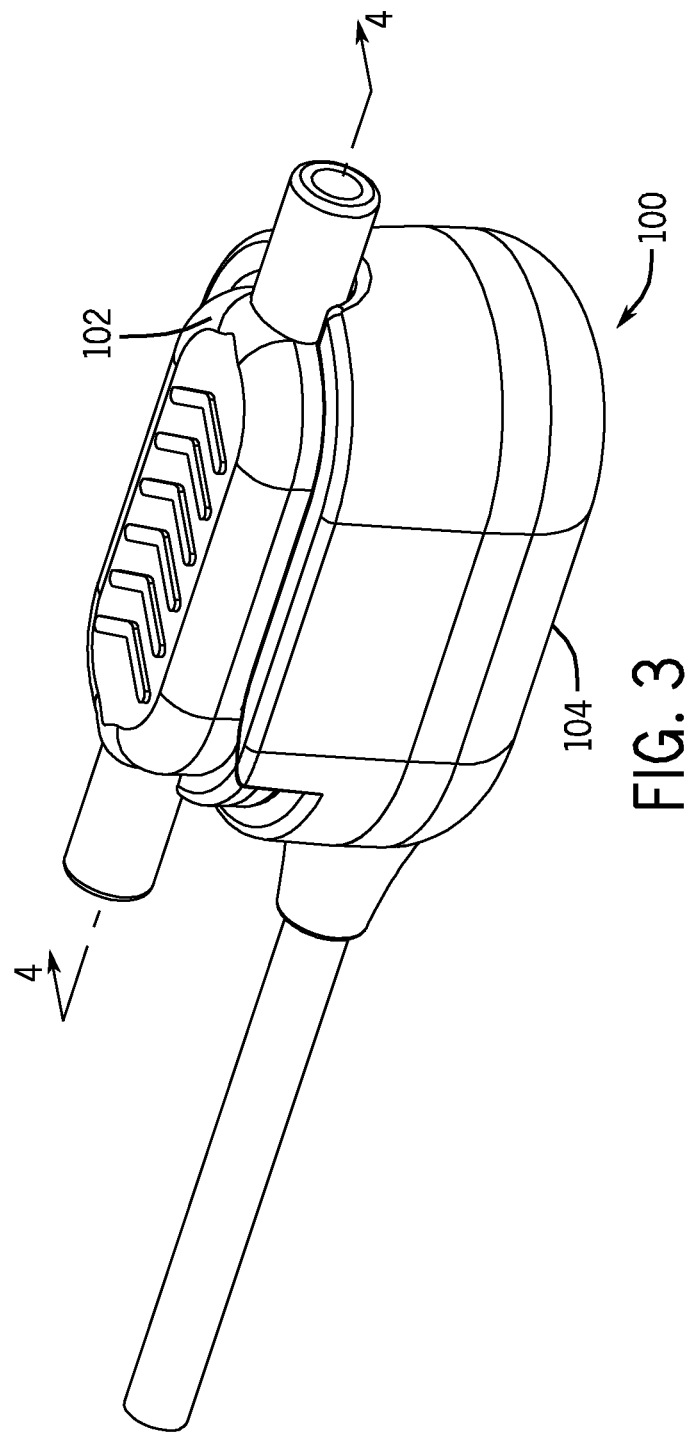
FIG. 3 is an isometric view of a differential pressure based flow sensor assembly of the embodiment of FIG. 1.
Figure 4:
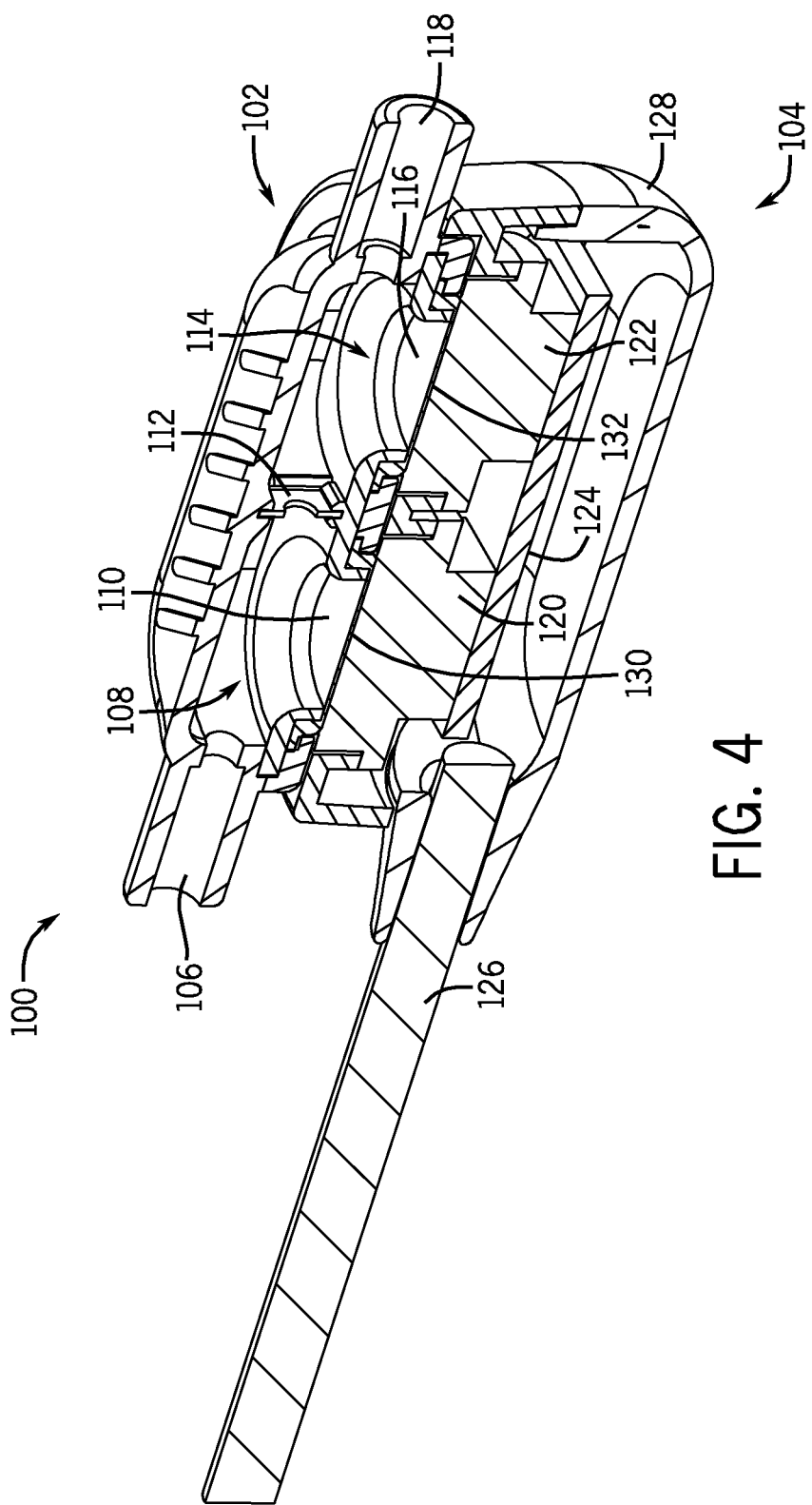
FIG. 4 is a cross-sectional view taken along line 4-4 of FIG. 3.

Turning next to FIG. 3 and FIG. 4, the differential pressure based flow sensor assembly 100 is shown in additional detail. The differential pressure based flow sensor assembly 100 has a disposable portion 102 and a reusable portion 104. As used herein reusable is defined as a component that is capable of being safely reused. For example, the same reusable portion 104 can be used multiple times on the same patient with the disposable portion 102 being changed at least every 72 hours or so. The same reusable portion 104 can be used hundreds or even thousands of times on different patients, subject to the cleaning policies recommended by the manufacturer or the healthcare institution, by installing a new disposable portion 102. This is possible since the reusable portion 104 is designed to prevent fluid ingress. As may best be seen in FIG. 4, the disposable portion 102 has a fluid inlet 106 an upstream fluid chamber 108, an upstream fluid pressure membrane 110, a flow restricting element 112, a downstream fluid chamber 114, a downstream fluid pressure membrane 116, and a fluid outlet 118. The membranes 110 and 116 are fluid impermeable. Although full membranes are shown, it is contemplated that other types of seals, including but not limited to one or more gaskets and O-rings, would suffice to keep fluid out of the housing of the reusable portion. Any exposed areas could be swabbed with a cleaning solution, if necessary.

As shown in FIG. 4, medication enters the disposable portion 102 through the fluid inlet 106. The medication flows into the upstream fluid chamber 108 from the fluid inlet 106. Next, the medication flows through the flow restricting element 112 and into the downstream fluid chamber 114. The flow of the medication through the flow restricting element 112 results in a drop in fluid pressure as the fluid flows from the upstream fluid chamber 108 to the downstream fluid chamber 114 through the flow restricting element 112. Thus, during forward fluid flow under normal conditions, the fluid pressure within the upstream fluid chamber 108 is generally greater than the fluid pressure within the downstream fluid chamber 114. The fluid pressure within the upstream fluid chamber 108 presses against the upstream fluid pressure membrane 110. Similarly, the fluid pressure within the downstream fluid chamber 114 presses against the downstream fluid pressure membrane 116.

It is contemplated that a variety of materials may be utilized for the manufacture of the disposable portion 102. The disposable portion 102 may comprise a thermoplastic. It is contemplated that the flow restricting element 112 may be made of the same thermoplastic as the rest of the disposable portion 102, or may be a different material than the disposable portion 102. Non-limiting examples of the material that may be utilized to form the flow restricting element 112 include silicon, glass, and medical grade thermoplastics and elastomerics. The fluid pressure membranes 110, 116 may comprise a variety of polymers or elastomers, such as TPE, or silicone.

It is additionally contemplated that the flow restricting element 112 may be formed integrally with the rest of the disposable portion 102, or the flow restricting element 112 may be a separate component placed within the disposable portion 102.

As may also be seen in FIG. 4, the reusable portion 104 of the differential pressure based flow rate sensor assembly 100 has an upstream pressure sensor 120, a downstream pressure sensor 122, a circuit board 124, and an electrical connection 126, all contained within a housing 128. The upstream pressure sensor 120 is adapted to interact with the upstream fluid pressure membrane 110 to generate a reading of fluid pressure within the upstream fluid chamber 108. Similarly, the downstream pressure sensor 122 is adapted to interact with the downstream fluid pressure membrane 116 to generate a reading of fluid pressure within the downstream fluid chamber 114. The circuit board 124 receives output from both the upstream pressure sensor 120 and the downstream pressure sensor 122. The circuit board 124 may calculate a pressure difference between the upstream fluid chamber 108 and the downstream fluid chamber 114, or the circuit board 126 may generate an output signal that is transmitted to another device with a processor, such as the infusion pump 12, that calculates the pressure difference between the upstream chamber 108 and the downstream chamber 114. Output of the circuit board 124 passes through electrical connection 126 to the infusion pump 12 (FIG. 1).

Although a wired electrical connection 126 is shown in FIG. 4, the system may optionally comprise wireless electrical connection and communication with the infusion pump 12 or other system components. It is additionally contemplated that according to some alternative embodiments, the reusable portion 104 may further contain additional electronics, such as, batteries, one or more memories, amplifiers, signal conditioning components, analog-to-digital converters, power converters, LED indicators, a display, sound generating components, a wireless communication engine, inductive coils for receiving power from the infusion pump 12 or another source, and active or passive radio frequency identification devices (RFID). It will be appreciated that the calculations and processing described herein can take place on the circuit board 124, in the infusion pump 12, in a remote processor (not shown), or be concentrated in only one of the system components, or distributed among one or more of the system components as needed or desired.

The components of the reusable portion 104 are contained within the housing 128. The housing 128 may be manufactured from a polymeric material such as polycarbonate, polyethylene, polyurethane, polypropylene, acrylic, or other known materials. It is further contemplated that an upstream reusable portion membrane 130 may separate the upstream fluid pressure membrane 110 from the upstream fluid pressure sensor 120. Likewise, a downstream reusable portion membrane 132 may separate the downstream fluid pressure membrane 116 from the downstream fluid pressure sensor 122.

Figure 5A:
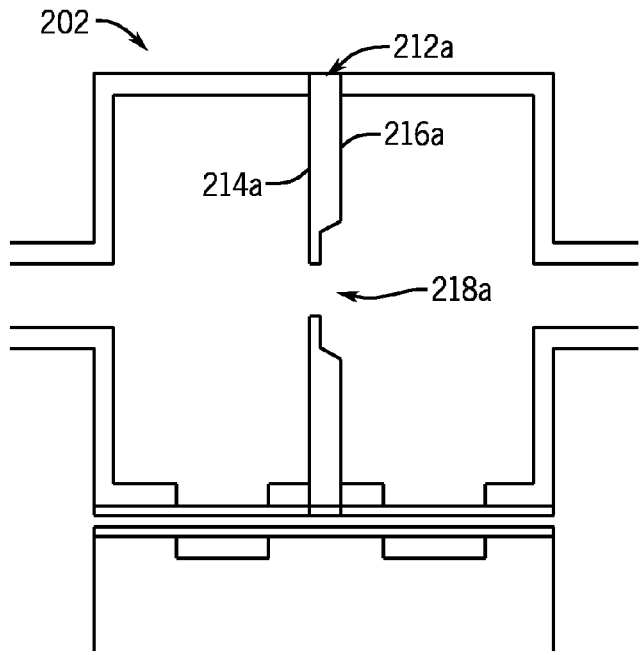
FIGS. 5a-5e illustrate cross-sections of flow restricting elements within differential pressure based flow sensor assemblies according to various embodiments.
Figures 5B, 5C, 5D, 5E:
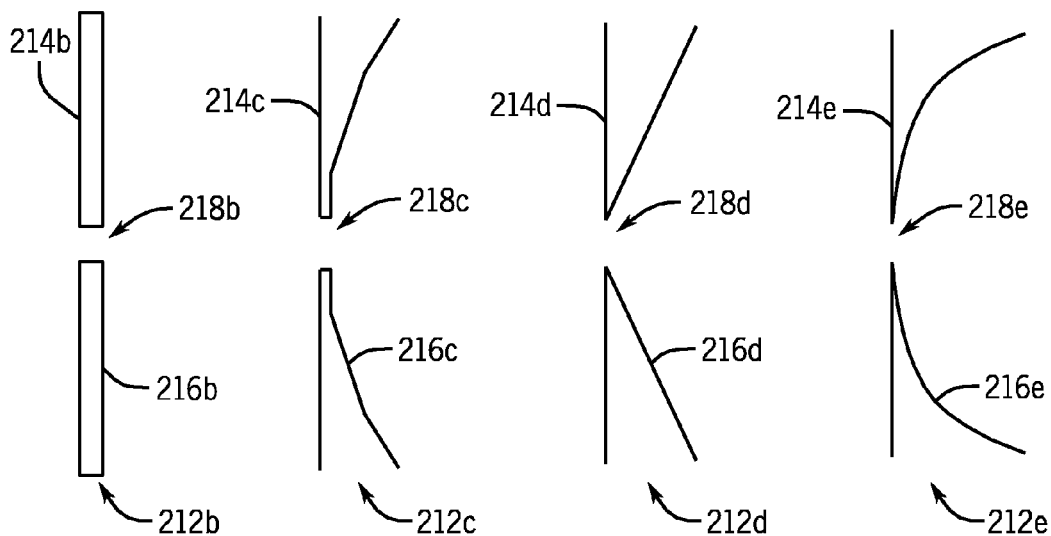

Referring next to FIG. 5a, a cross-section of a disposable portion 202 is schematically illustrated with a flow restricting element 212a to illustrate the profile of the flow restricting element 212a. The flow restricting element 212a may be identical to the flow restricting element 112, but may also vary. The flow restricting element 212a is in the form of an orifice. An orifice may be a beneficial flow restricting element, as orifice performance varies less between fluids of different viscosities than other flow restricting elements, such as capillary channels. That is to say, the measured pressure differential across an orifice for a given flow rate will be largely independent of the viscosity of the active solution, where the pressure difference measured across alternate restrictions such as capillaries will demonstrate a strong dependence upon fluid viscosity. The flow restricting element 212a has a front face 214a located on an upstream side of the flow restricting element 212a, and a rear face 216a on the downstream side of the flow restricting element 212a. An opening 218a is formed through the flow restricting element 212a to allow fluid to flow through the flow restricting element 212a.

The opening 218a may have a variety of cross-sectional shapes, but a circular opening is commonly used. In order to help reduce the effect of fluid viscosity on the flow of the fluid through the opening 218a of the flow restricting element 212a, the opening 218a may have a ratio of a perimeter of the opening 218a to the length the fluid travels though the opening 218a of from about 1:1 to about 1000:1. That is, the perimeter of the opening is sufficiently larger than the length of fluid flow though the opening 218a, such that the pressure drop through the opening 218a is less dependent on the fluid, and more dependent on the geometry of the opening 218a. An opening 218a having a perimeter to flow length ratio of about 100:1 has been found to be effective. For example, a 430 micron diameter circular orifice with a length in the flow dimension of 12 microns will accommodate flow rates in the hundreds to thousands of ml/hr. A smaller diameter orifice would be needed for smaller flow rates and associated applications.

The thickness of the opening 218a of the flow restricting element may vary from about 5 microns to about 25 microns. An opening 218a having a thickness of about 12 microns has been found to be effective. In order to demonstrate the desired flow characteristics, it is important to provide a flow orifice or opening in a solid geometry. The ratio of the inlet height to the effective hydraulic diameter of the orifice should be rather large, such as at least 10:4 or about 5:1. However, a constant-thickness membrane, of thickness equal to the length of the desired orifice, may become mechanically weak if the overall area of the membrane is large. Once the orifice opening is established, the membrane material in which the orifice resides can be thicker as one moves away from the orifice perimeter. As a result, the orifice itself can provide the desired restrictive fluid path length, while the membrane in which the orifice resides is thicker than the length of the orifice at a location away from the orifice. Thus, it is contemplated that various other geometries may also be used to form a flow restricting element.

As shown in FIG. 5a, the flow restricting element 212a transitions from a thicker cross sectional shape to a thinner cross sectional shape near the opening 218a. Creating such geometry for the flow restricting element 212a allows for various low cost manufacturing approaches for the flow restricting element 212a. Creating such geometry has a limited effect on performance of the flow restricting element 212a, as such geometry does not introduce a significant pressure difference for fluids having different viscosities, but having the same fluid flow rate. Thus, the thinness of the flow restricting element 212a near the opening 218a limits the effect of fluid viscosity on pressure drop through the opening 218a, while thicker material away from the opening 218a increases the overall strength of the flow restricting element 212a.

FIGS. 5b-5e illustrate alternative flow restricting elements 212b-212e that function similarly to flow restricting element 212a. Flow restricting element 212b maintains a constant thickness, while flow restricting elements 212c-212e are thinner near the openings 218c-218e. The geometry of the rear face 216a-216e does not have a great effect on flow characteristics through openings 218a-218e. This is because flow through the opening 218a-218e typically features well-defined fluid velocity profiles with minimal fluid/wall dynamic interaction on the orifice backside, as long as the rear face 216a-216e geometry is sloped away from the orifice appropriately, and therefore minimizes viscosity induced pressure losses. Some of these orifice geometries lend themselves to manufacturing advantages. For example, orifice 218a can be formed efficiently via silicon processing techniques such as etching, lithography, masking and other MEMS operations. Orifice 218b can be formed efficiently by laser machining thin flat stock material. Orifices 218c and 218d could be formed easily with photo-imaging glass processing techniques. Orifices 218c, 218d, and 218e could be formed using molding or embossing techniques. Further combinations of techniques could be utilized within the scope of the invention.

While many embodiments have been described in connection with an upstream pressure sensor, a flow restricting element, and a downstream pressure sensor within a common assembly, it is further contemplated according to a further alternative embodiment, that these components may be separate standalone components within a fluid flow system. The methods and processes of measuring fluid flow rates and the volume of fluid flow are generally identical to those previously described according to this alternative embodiment. Thus, by monitoring the difference in pressure between a standalone upstream pressure sensor and a standalone downstream pressure sensor generated by fluid flowing through a standalone flow restricting element, the fluid flow rate may be calculated.

Turning next to FIG. 6, an IV push or bolus is shown being delivered to the patient 10. The caregiver 26 connects the syringe 24 to the second fluid line segment 18 via the connection 20. The caregiver 26 then delivers the mediation within the syringe 24 to the patient through the connection 20. The medication passes through the differential pressure based fluid flow sensor 100 and the third fluid line segment 22 to the patient 10. The differential pressure based fluid sensor assembly 100 monitors the flow rate of the medication through the sensor assembly 100. By monitoring the flow rate through the sensor assembly 100, the volume of medication delivered to the patient 10 may be calculated.

The flow rate of the fluid through the pressure sensor assembly 100 may be calculated by the following equation:

$$Q = AC_D \sqrt{\frac{2\Delta P}{\rho}},$$

where Q is the volumetric flow rate, ΔP is the pressure differential between an upstream pressure sensor and a downstream pressure sensor, ρ is the fluid mass density, $C_D$ is an opening discharge coefficient, and A is the area of the opening. The use of an orifice for the opening has been empirically shown to minimize the dependence of the induced pressure differential on fluid viscosity, and the discharge coefficient remains essentially constant, thus making the flow rate a function of pressure, density, and area.

Once the flow rate Q has been calculated, the volume of the flow may be determined by integrating the flow rate over a period of time using the following equation: V=∫Qdt. Using this equation, both forward and backward flow thorough the sensor assembly 100 may be calculated. A negative flow rate would indicate that the pressure at the downstream sensor 122 is higher than the pressure at the upstream sensor 120, and thus fluid is flowing backwards through the sensor assembly 100, away from the patient 10.

In order to provide a more accurate ΔP, a pressure tare, or calibration of the sensors, may be performed, preferably in a zero flow condition. A pressure tare subtracts the average pressure of both the upstream pressure sensor 120 and the downstream pressure sensor 122 from the readings of the respective upstream and downstream pressure sensors 120, 122 during fluid delivery. Utilizing such a pressure tare reduces the occurrence of signal drifts from pressure supply drifts, amplification, temperature variance, or residual pressures from any priming steps prior to delivering and recording a bolus dose.

Reverse flow of fluid through the sensor can be also measured with ΔP being negative. In this case, the flow is computed by taking the absolute value of ΔP and moving the negative sign outside the square root, $$Q = -AC_D \sqrt{\frac{2|\Delta P|}{\rho}}.$$

Negative flow rates are important to aggregate in the computation of true net forward volume delivery from the syringe, as they may impact the accuracy of total net volume delivered from the syringe. Additionally, an occlusion condition (i.e., the catheter 25 or the patient's vein being closed or occluded) can be detected using a back draw of the syringe prior to forward fluid delivery, a typical clinical practice. Under normal conditions, reverse flow of the fluid can be directly measured and aggregated into the net forward volume delivery. However, under occlusion scenarios, the occluded reverse flow can be quickly detected by the sensor using threshold negative limits of the downstream and upstream sensors drawing a negative vacuum pressure.

The outputs of the upstream pressure sensor 120 and the downstream pressure sensor 122 may further be monitored for detection of motion artifacts to distinguish such artifacts from true flow patterns. To detect motion artifacts, a ratio of the upstream pressure sensor 120 output to the downstream pressure sensor 122 output is monitored. If, for example, the ratio is less than a predetermined threshold, such as 3:1, it is likely that any changes in pressure indicated by the upstream pressure sensor 120 and the downstream pressure sensor 122 are the results of motion artifacts within the sensor assembly 100, not forward fluid flow. Thus, flow is only indicated when the ratio of the pressures indicated by the upstream pressure sensor 120 and the downstream pressure sensor 122 is greater than a threshold amount. This is because once flow is initiated, the flow restricting element 112 causes the pressure at the upstream pressure sensor 120 to be significantly higher than the pressure at the downstream pressure sensor 122. Alternatively, reverse fluid flow is similarly distinguished from motion artifacts, if the ratio of the downstream pressure sensor to the upstream pressure sensor is less than a limit threshold, such as 3:1, and otherwise the signal is considered motion artifacts. Pressure values obtained due to motion artifacts may be excluded from the flow rates and aggregate volume computation. Motion artifacts events are also distinguished from events indicating the true onset of flow, which is used to gate or determine the start of bolus delivery via the syringe 24.

Algorithms also are contemplated to detect the start and end of a single bolus dose. Such an algorithm may rely on a first derivative and a short term mean value of the flow rate. If the mean value of the flow rate is above a certain threshold, such as for example 300 ml/hr, and the mean value of the derivative of the flow rate is above another threshold value, such as 50 (ml/hr)/sec, this flow rate and flow rate derivative indicate a start of a bolus dose. The threshold values are selected based upon the finding that typical bolus dose deliveries have a flow rate between about 300 ml/hr to about 5000 ml/hr, while a human injecting a bolus dose is typically incapable of delivering the injection at a rate less than about 50 ml/hr, on a per second basis.

The outputs of the differential pressure sensor assembly 100 may also be used to monitor both the delivery of medication via a single bolus dose, and via an infusion pump. Such an algorithm would indicate that a flow rate below a threshold level, such as for example 300 ml/hr, is not from a bolus dose. Similarly, infusion pump cycles provide a consistent sinusoidal pattern of deliveries with every pumping cycle. Utilizing an approach that analyzes the output of the sensor assembly 100 in a frequency domain, such as through a Fourier transform, pump infusion cycles appear at a much higher frequency than flow rates introduced through a single bolus dose. A low pass filter with a cutoff frequency separating the frequency band due to an infusion pump action, versus manual delivery via a single bolus dose, can segregate the flow rate signal due to each source. Alternatively, an inverse Fourier transform of the frequencies in the band below the frequencies affected by the pump action can recover a time domain flow rate signal from the differential pressure based sensor assembly 100 to quantify the amount of flow from a single bolus dose. Such an algorithm to isolate flow due to a pump source from flow due to manual injection could also be utilized to verify an infusion pump flow rate. Similarly, pressure pulsations occurring as a result of arterial pulsations when the sensor is in direct fluidic connection with an arterial vessel can be detected and mathematically compensated for using frequency domain low pass filtering below a cutoff frequency, since manual injections are usually lower frequency than arterial pulsations. Alternatively, linear weighted averaging of pressure values measured at the sensor is a form of filtering or smoothing that can be applied on the signal to reduce the effect of pulsations. Typical infusion pumps do not measure flow volume, but rather estimate flow volume based upon pump fluidic displacement. Thus, a differential pressure based flow sensor assembly 100 may verify infusion pump function, or be used in a closed feedback loop to control pump flow rate.

Yet another algorithm contemplated allows the differential pressure based sensor assembly 100 to be used to detect air pockets within fluids flowing through the sensor assembly 100. An air pocket typically is much less dense than a fluid passing through the sensor assembly 100. Thus, an air pocket or bubble within a fluid medium generates an abrupt change in pressure value, followed by a return to expected levels. The start and end of the abrupt change in pressure values is detected by monitoring the first derivative and the second derivative of the output of the upstream pressure sensor 120 and the downstream pressure sensor 122. An abrupt change in pressure would first be noticed on the upstream pressure sensor 120, followed by an abrupt change in pressure on the downstream pressure sensor 122. These pressure changes would be followed by an abrupt resumption back to pressure levels prior to air pocket reception, once the air pocket is passed. The duration of the deviation from typical pressures is indicative of the size of the air pocket.

Figure 7:
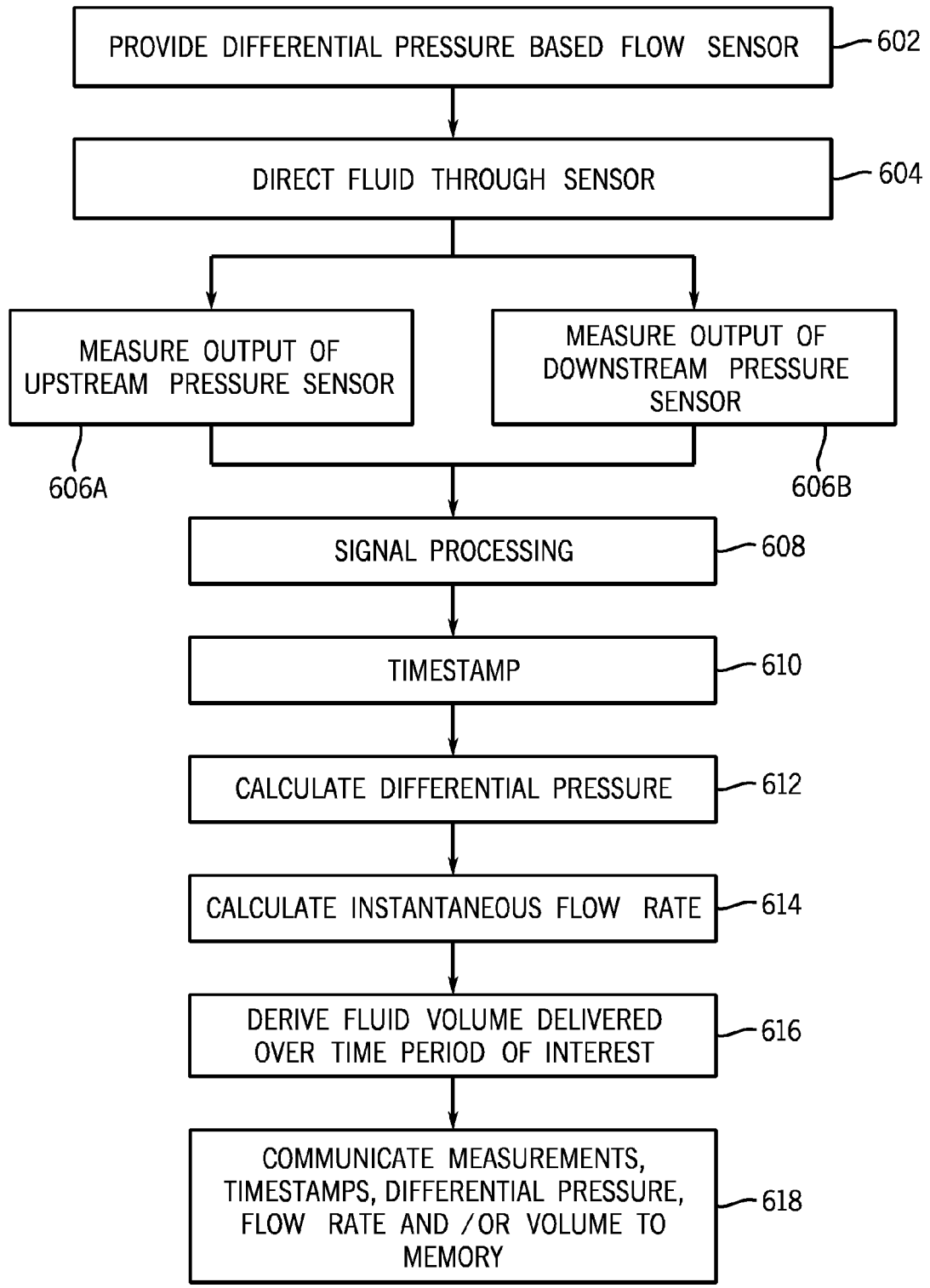
FIG. 7 schematically illustrates a method of delivering medication using a system having a differential pressure based flow sensor assembly according to one basic process.

FIG. 7 shows a basic process of utilizing a differential pressure based sensor assembly 100 to determine the instantaneous flow rate and/or volume of a fluid flow delivered through a bolus or other delivery. The process provides a differential pressure based flow sensor assembly 100 in step 602. Fluid flows through the sensor assembly in step 604. The output of the upstream pressure sensor 120 is measured in step 606A, and the output of the downstream pressure sensor 122 is measured in step 606B. The signals from the sensors 120, 122 can be filtered, amplified, or otherwise processed (for example as described above) in step 608. A timestamp is associated with the measurements in step 610. A differential pressure is calculated based upon the observed measurements in step 612. The instantaneous fluid flow rate is calculated in step 614. The flow rate is integrated over time to derive the volume delivered during the time period of interest in step 616. In step 618, the sensor signals or measurements, timestamp information, differential pressure, flow rate and/or volume delivered are communicated to a memory, which can be located in the sensor assembly 100, in the infusion pump 12, or another computer.

Figure 7A:
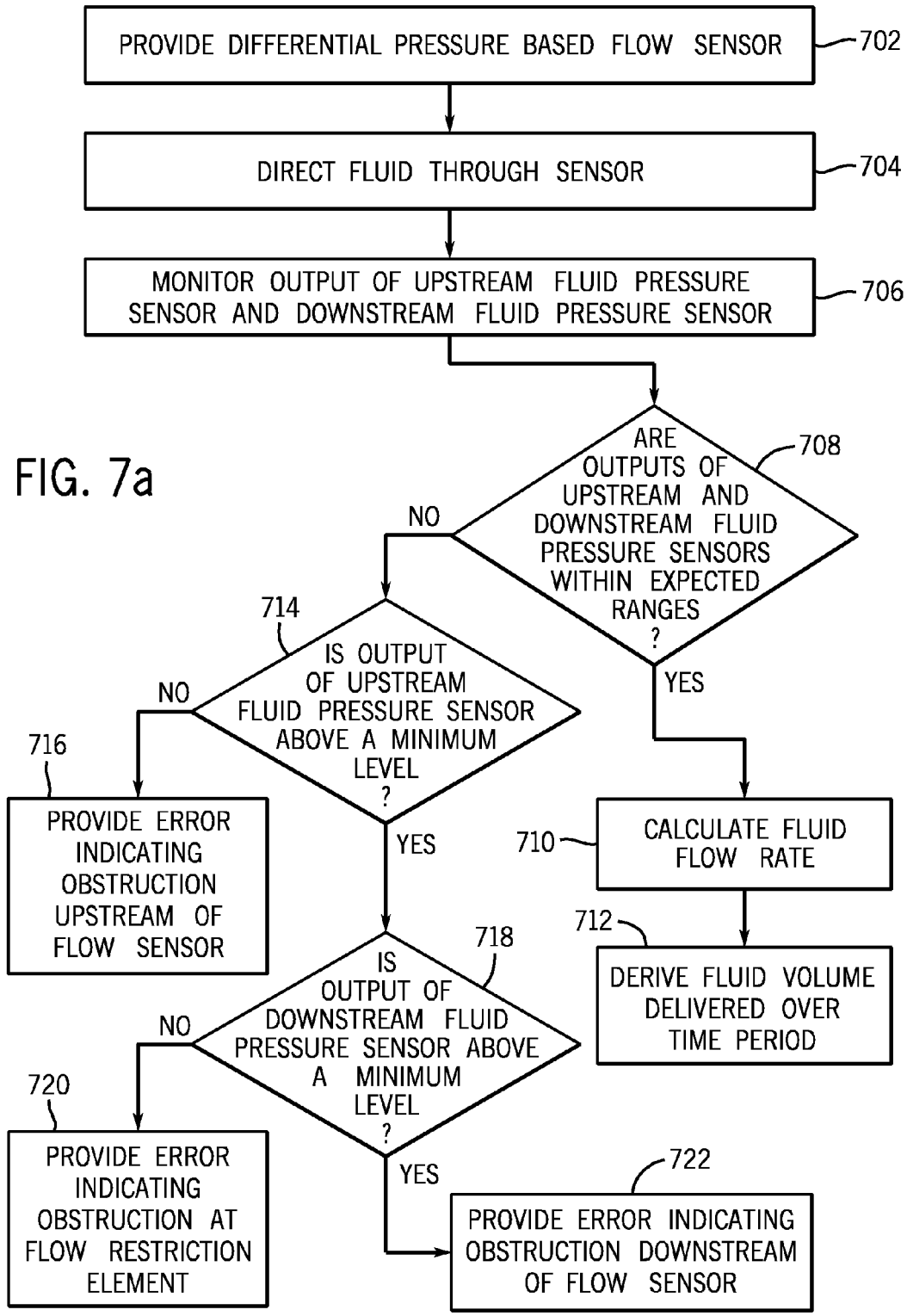
FIG. 7a schematically illustrates a method of delivering medication using a system with a differential pressure based flow sensor assembly, according to a more elaborate process than FIG. 7; and, FIGS. 8a-8b schematically illustrate a method of delivering medication using a system having a differential pressure based flow sensor assembly according to another process.

Turning now to FIG. 7a, a process of utilizing a differential pressure based sensor assembly to deliver a fluid is depicted, including monitoring for possible occlusions within the delivery system. The process provides a differential pressure based flow sensor in step 702. Fluid flows through the sensor in step 704 and the output of both the upstream fluid pressure sensor and the downstream fluid pressure sensor are monitored in step 706. The process determines whether the outputs of both the upstream fluid pressure sensor and the downstream fluid pressure sensor are within expected ranges in step 708. If so, the process calculates the fluid flow rate, utilizing the algorithm previously described, in step 710. Once the flow rate has been determined, the process derives the volume that has passed through the sensor assembly 100 over a given period of time in step 712. As described above with respect to FIG. 7, the sensor signals or measurements, timestamp information, differential pressure, flow rate and/or volume delivered are communicated to a memory, which can be located in the sensor assembly 100, in the infusion pump 12, or another computer or processor.

If the outputs of the upstream and downstream fluid pressure sensors do not fall within expected ranges, the process determines if the output of the upstream fluid pressure sensor is above a minimum level in step 714. If the pressure is not above a preset minimum level, an error signal is generated in step 716, indicating that a possible obstruction exists upstream of the differential pressure based flow sensor assembly 100. However, if the output of the upstream fluid pressure sensor is above a minimum level, the process in step 718 determines if the output level of the downstream fluid pressure sensor is above a preset minimum level. If the output of the downstream fluid pressure sensor is not above a preset minimum level, an error signal is generated in step 720 that indicates an obstruction may be present at the flow restricting element 112. However, if the downstream fluid pressure sensor detects a pressure above the preset minimum level, an error signal is generated in step 722 indicating that an obstruction may be present downstream of the differential pressure based flow sensor assembly 100.

Thus, utilizing the process illustrated in FIG. 7a, the flow rate of a fluid as well as the volume of the fluid delivered through a differential pressure based flow sensor assembly may be calculated, and an error message may be provided when an occlusion occurs.

Figure 8A:
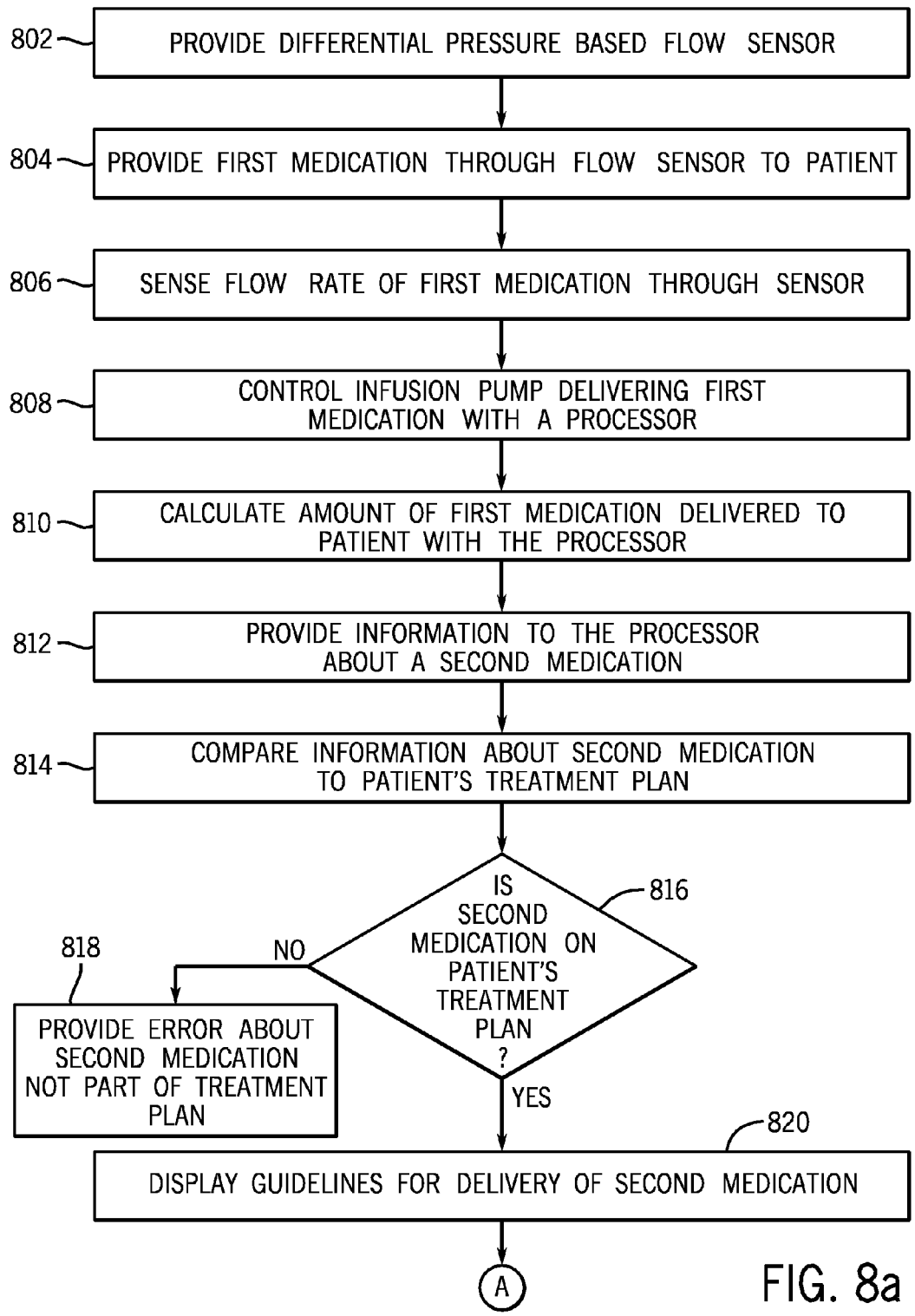
Figure 8B:
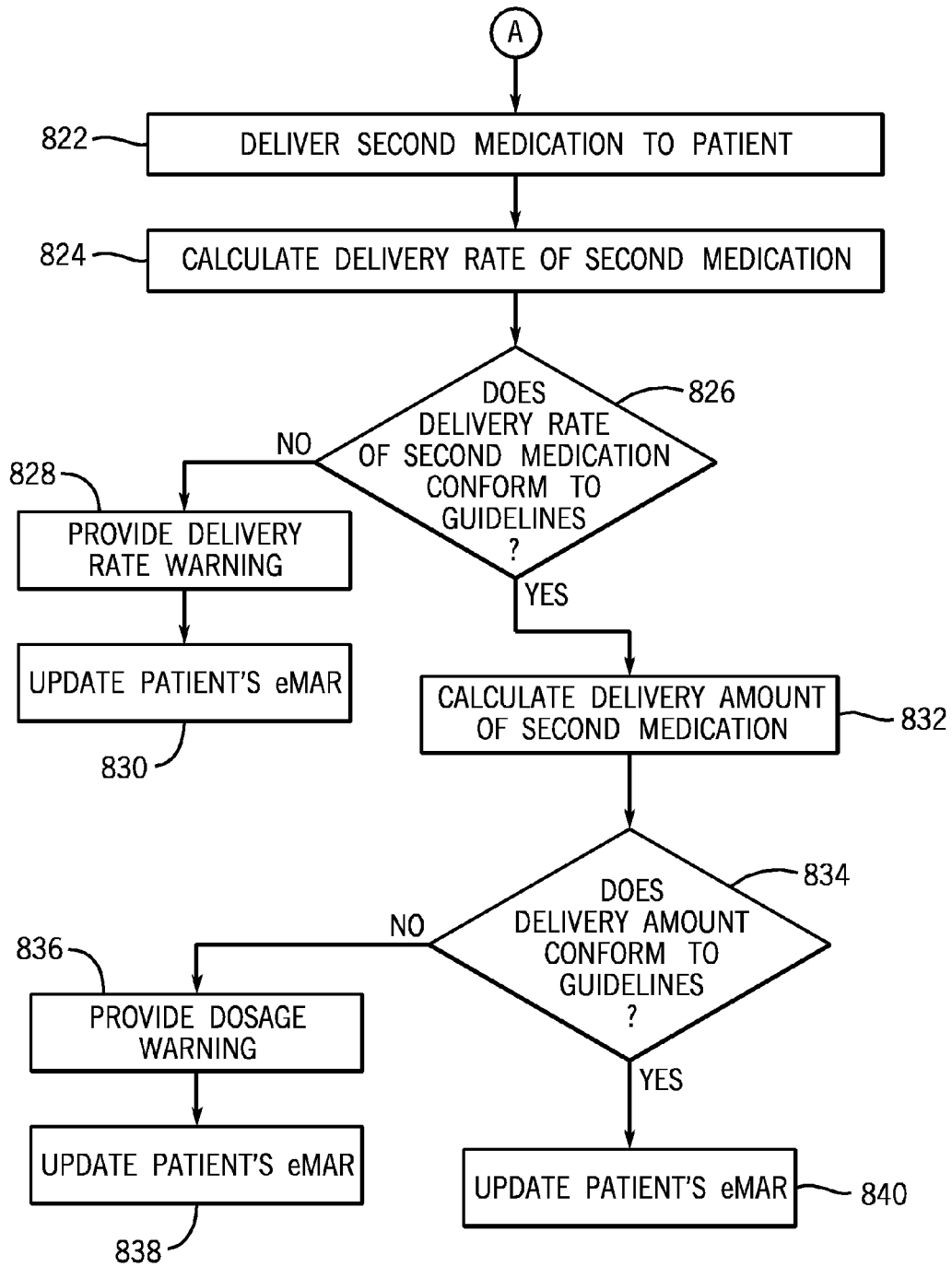

As shown in FIGS. 8a-8b, a method of delivering medication to a patient utilizing a medication delivery system having an infusion pump is depicted in block diagram form. The process provides a differential pressure based flow sensor assembly in step 802, such as sensor assembly 100 previously described herein. A first medication is provided through the flow sensor assembly to the patient 10 in step 804. The flow through the sensor assembly is sensed in step 806. In step 808, the process controls an infusion pump delivering the first medication via a processor. The amount or volume of the first medication delivered to the patient is calculated in step 810 using the processor and signals received from the differential pressure based flow sensor assembly 100. Information about a second medication to be delivered to the patient is provided to the processor in step 812. The information provided about the second medication is compared to information within the patient's treatment plan in step 814. The process determines in step 816 whether the second medication is on the patient's specific treatment plan, such as by checking whether the patient has a medical order or prescription for the second medication. If the second medication is not found on the patient's treatment plan, an error message is provided in step 818 indicating that the second medication is not found on the patient's treatment plan, and the caregiver should check with a physician or other caregiver to determine if it is appropriate to provide the second medication to the patient. If the second medication is found on the patient's treatment plan, guidelines for delivering the second medication are generated or displayed in step 820. The guidelines can include but are not limited to a target delivery rate with upper and/or lower limits, a total volume or amount to be delivered during the bolus, and a time period over which to deliver the IV push or bolus.

Continuing now to FIG. 8b, the second medication is delivered to the patient in step 822. The process calculates the delivery rate of the second medication using the differential pressure based flow rate sensor assembly 100 in step 824. As described with respect to FIG. 7 above, the delivery flow rate calculations can be stored in memory. A comparison is performed in step 826 to determine if the delivery rate of the second medication conforms to the delivery guidelines. If the delivery rate does not conform to the delivery guidelines, a delivery rate warning is provided to the caregiver in step 828. If the delivery rate warning is provided, the patient's electronic medication administration record (eMAR) is updated in step 830 to show that the second medication was delivered at a rate inconsistent with the delivery guidelines or protocols. The amount of the second medication delivered to the patient can also be calculated in step 832. The process in step 834 compares the amount of the second medication delivered to the amount of the second medication the patient was scheduled to receive. If the amount of the second medication the patient received does not conform to the patient's treatment plan, a dosage warning is provided to the caregiver at step 836. This warning can indicate that the patient was provided an underdose of the second medication, or that the patient was provided with an overdose of the second medication. The patient's electronic medication administration record (eMAR) is updated in step 838 to include the amount of the second medication that was provided to the patient, as well as information to indicate that the dosage of the second medication did not conform to the patient's treatment plan. If the amount of the second medication delivered to the patient conforms to the patient specific guidelines, the patient's electronic medication administration record (eMAR) is updated in step 840 to indicate that a proper dosage of the second medication was delivered to the patient. It is contemplated that every update to the patient's electronic medication administration record (eMAR) will note the time a medication was delivered to the patient, as well as the caregiver responsible for delivering that medication to the patient.

According to a further embodiment, a disposable infusion tubing set is provided that has a disposable portion of a differential pressure based flow sensor assembly. The tubing set would include at least a first tube adapted to connect to a first medication reservoir, and a connection site to allow a second medication to be introduced into the first tube of the tubing set upstream of the disposable portion of the differential pressure based flow sensor assembly. The disposable infusion tubing set further has a second tube adapted to connect to a patient access device. The second tube is adapted to be positioned downstream of the disposable portion of the differential pressure based flow sensor assembly. As discussed above, the disposable portion of the differential pressure based flow sensor assembly can be disposed in other locations within the disposable infusion tubing set, depending on the line pressure conditions, delivery flow rates, or fluid volume delivery amounts of interest.

According to yet another embodiment, a differential pressure based flow rate sensor assembly is replaced by a pressure based event detection sensor. A pressure based event detection sensor allows an event, such as a bolus, to be detected noting a spike in pressure. Such an event detection sensor would not allow the computation of the volume of medication delivered, but will place a notation onto a patient's record that some medication was delivered at a specific time. Thus, a record will exist confirming that a patient was provided with medication.

According to yet a further embodiment, a differential pressure based flow sensor assembly may be powered by an inductive power source. Such an embodiment would contain many of the same features as the differential pressure based flow sensor assembly 100 described herein. Similarly, it is contemplated that a wireless differential pressure based flow sensor assembly may transmit information regarding a pressure at an upstream pressure sensor and information regarding a downstream pressure sensor to other components within a system. Finally, it is contemplated that the portion 104 of the differential pressure based flow sensor assembly 100 could be produced using MEMS, integrated circuits or other technology in a miniaturized and low cost manner, such that the portion 104 might be considered disposable as well.

While the foregoing has described what are considered to be the best mode and/or other examples, it is understood that various modifications may be made and that the subject matter disclosed herein may be implemented in various forms and examples, and that they may be applied in numerous other applications, combinations and environments, only some of which have been described herein. Those of ordinary skill in that art will recognize that the disclosed aspects may be altered or amended without departing from the true scope of the subject matter. Therefore, the subject matter is not limited to the specific details, exhibits and illustrated examples in this description. It is intended to protect any and all modifications and variations that fall within the true scope of the advantageous concepts disclosed herein.

We claim:

1. A differential pressure based flow sensor assembly to determine a flow rate of a fluid system comprising:
   a disposable portion having:
      a sealed disposable body defining a fluid flow passage forming an inlet and an outlet;
      a flow restricting element positioned along the fluid flow passage between the inlet and the outlet, wherein the flow restricting element includes an orifice that defines a fluid flow path;
      an impermeable fluid pressure membrane comprising:
         an upstream fluid pressure membrane at a location in the fluid flow passage between the inlet and the flow restricting element; and
         a downstream fluid pressure membrane at a location in the fluid flow passage between the flow restricting element and the outlet; and
   a reusable portion including a housing removably coupled to the disposable portion and comprising:
      an upstream fluid pressure sensor to sense an upstream fluid pressure at an upstream location in the fluid flow passage between the inlet and the flow restricting element, the upstream fluid pressure sensor being positioned and adapted to interact with the upstream fluid pressure membrane to determine the fluid pressure at the upstream fluid pressure membrane; and
      a downstream fluid pressure sensor to sense a downstream fluid pressure at a downstream location in the fluid flow passage between the flow restricting element and the outlet, the downstream fluid pressure sensor being positioned and adapted to interact with the downstream fluid pressure membrane to determine the fluid pressure at the downstream fluid pressure membrane;
   wherein the flow restricting element is a separate component secured within the disposable body between the upstream fluid pressure membrane and the downstream fluid pressure membrane.

2. The differential pressure based flow sensor assembly of claim 1, wherein the upstream fluid pressure membrane and the downstream fluid pressure membrane comprise an elastomeric material.

3. The differential pressure based flow sensor assembly of claim 1, wherein the orifice defines a non-capillary fluid flow path.

4. A fluid-tight disposable assembly for removably dry coupling to a reusable portion of a differential pressure based fluid flow sensor assembly, the disposable assembly comprising:
   a sealed disposable body defining a fluid flow passage forming an inlet and an outlet;
   a flow restricting element positioned along the fluid flow passage between the inlet and the outlet, wherein the flow restricting element includes an orifice that defines a fluid flow path;
   an impermeable fluid pressure membrane comprising:
      an impermeable upstream fluid pressure membrane sealing an upstream fluid chamber at a location in the fluid flow passage between the inlet and the flow restricting element; and an impermeable downstream fluid pressure membrane sealing a downstream fluid chamber at a location in the fluid flow passage between the flow restricting element and the outlet;

wherein the flow restricting element is a separate component secured within the body between the upstream fluid pressure membrane and the downstream fluid pressure membrane.

5. A method of determining a fluid flow rate in a fluid flow system comprising:

providing a differential pressure based flow sensor assembly according to claim 1;

directing a fluid through the fluid flow passage; and calculating the fluid flow rate based on a pressure difference between an output of the upstream fluid pressure sensor and an output of the downstream fluid pressure sensor.

6. The method of determining a fluid flow in a fluid flow system of claim 5, further comprising deriving a fluid volume delivered over time based upon the calculating of the fluid flow rate.

7. A fluid delivery system for delivering medication from a first source to a patient including measuring a flow rate of the fluid, the system comprising:

an infusion pump that selectively varies a rate of flow of the first medication from the first source through a fluid line;

a differential pressure based flow sensor assembly according to claim 1 and adapted to determine the flow rate of the first medication within the fluid line; and a processor adapted to control the infusion pump by varying the rate of flow of the first medication based on information provided by the differential pressure based flow sensor assembly, the processor further being adapted to determine the amount of the first medication provided to the patient.

8. The system of claim 7 further comprising: a user input device in communication with the processor, the user input device being adapted allow a user to provide information regarding the first medication.

9. The system of claim 8, wherein the processor is adapted to compare information about the first medication received from the user input device to patient treatment information for the patient.

10. The system of claim 9, wherein the processor is adapted to update the patient treatment information for the patient based on information provided by the user input device and the differential pressure based flow sensor assembly.

11. The system of claim 7, wherein the fluid line is adapted to deliver the first medication from a reservoir to the patient, the fluid line further having a fitting adapted to deliver a second medication from a second source.

12. The system of claim 11, wherein the processor is adapted to determine the push rate of the second medication from the second source based on information provided by the differential pressure based flow sensor assembly, and wherein the second source is a syringe.

13. The system of claim 12, wherein the processor is adapted to compare the push rate of the second medication to patient treatment information for the patient.

14. A method of delivering medication to a patient comprising:

providing a differential pressure based flow sensor assembly according to claim 1 to determine a flow rate of a first medication within a fluid line;

sensing the flow rate of a first medication with the flow sensor assembly;

controlling an infusion pump that selectively varies the flow rate of the first medication, wherein the controlling is based upon information the flow sensor assembly provides a processor; and determining an amount of the first medication delivered to the patient, wherein the determining is based upon information the flow sensor assembly provides the processor.

15. The method of claim 14 further comprising:

delivering the first medication to the patient through a fluid line from a first source, the fluid line further having a fitting adapted to receive a second medication from a second source;

delivering a second medication to the patient from the second source via the fitting; and determining an amount of the second medication delivered to the patient, wherein the determining is based upon information the flow sensor assembly provides the processor; and calculating the delivery rate of the second medication, wherein the calculating is based upon information the flow sensor assembly provides the processor.

16. The method of claim 15 further comprising:

sending information about the first medication or the second medication to the processor;

accessing patient specific treatment information with the processor;

comparing the information about the first medication or the second medication with patient specific information;

alerting a caregiver if either the first medication or the second medication is not located on the patient specific treatment information.

17. The method of claim 16 further comprising:

updating the patient specific treatment information to show the amount of the first medication and the second medication delivered to the patient.

18. The method of claim 16 further comprising:

generating guidelines for delivery of the second medication;

delivering a second medication to the patient from the second source via the fitting;

calculating the delivery rate of the second medication, wherein the calculating is based upon information the flow sensor assembly provides the processor alerting a caregiver if the delivery rate of the second medication does not generally conform to the generated guidelines for delivery of the second medication.

19. The method of claim 18 further comprising:

delivering a second medication to the patient from the second source via the fitting;

determining an amount of the second medication delivered to the patient, wherein the determining is based upon information the flow sensor assembly provides the processor; and alerting a caregiver if the amount of the second medication delivered to the patient does not generally conform to the patient specific treatment information.

* * * * *